(12) United States Patent
Duckett

(10) Patent No.: US 6,490,782 B1
(45) Date of Patent: Dec. 10, 2002

(54) AUTOMATED IN-LINE FILTER CHANGING APPARATUS

(75) Inventor: Gregory S. Duckett, Raleigh, NC (US)

(73) Assignee: Varian, Inc., Palo Alto, CA (US)

( * ) Notice: Subject to any disclaimer, the term of this patent is extended or adjusted under 35 U.S.C. 154(b) by 96 days.

(21) Appl. No.: 09/690,097

(22) Filed: Oct. 16, 2000

(51) Int. Cl.$^7$ ................................................ B23P 21/00
(52) U.S. Cl. ..................... 29/714; 221/221; 221/222; 198/724; 414/797.7
(58) Field of Search .................. 221/221, 222, 221/210, 211; 414/797.7; 29/785, 789, 714, 792, 786, 793; 53/235; 198/724; 422/101

(56) References Cited

U.S. PATENT DOCUMENTS

| | | | | |
|---|---|---|---|---|
| 1,634,566 | A | * | 7/1927 | Wessman |
| 2,527,471 | A | * | 10/1950 | Losberg |
| 2,721,016 | A | * | 10/1955 | Canales |
| 4,279,860 | A | | 7/1981 | Smolen |
| 4,924,716 | A | | 5/1990 | Schneider |
| 4,987,721 | A | * | 1/1991 | Turtschan |
| 5,011,662 | A | | 4/1991 | Noormohammadi et al. |
| 5,450,982 | A | | 9/1995 | Van Den Oever |
| 6,060,024 | A | | 5/2000 | Hutchins et al. |
| 6,322,110 | B1 | * | 11/2001 | Banker et al. |

* cited by examiner

Primary Examiner—David P. Bryant
Assistant Examiner—Steven A Blount

(57) ABSTRACT

An automated filter changing system comprises a rotatable filter dispensing assembly and a filter clamping assembly. The filter dispensing device receives filter storage magazines in which a plurality of filters are initially stored in the form of connected stacks. The filter dispensing assembly includes a filter separating device having a stationary portion. The filter separating device separates one or more stacks of filters into discrete filter units, such that individual filters are transported sequentially from the filter dispensing device. The filter clamping assembly operates in conjunction with the filter dispensing device to receive one or more individual filter units dispensed therefrom, and provides one or more coupling sites which can fluidly communicate with one or more fluid lines. The filter clamping device couples unused filters to fittings associated with the fluid lines by applying an evenly distributed force to the filters.

26 Claims, 13 Drawing Sheets

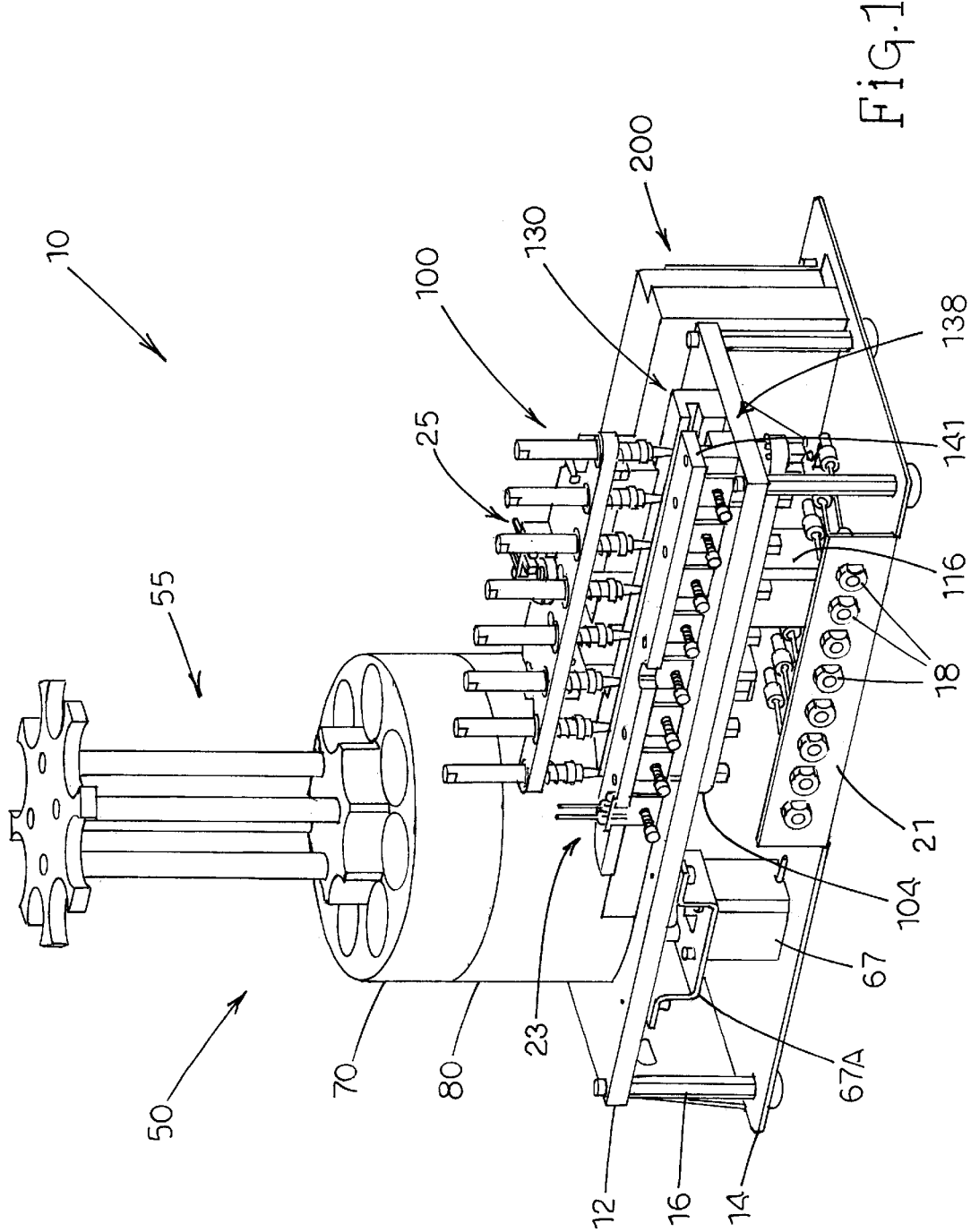

AUTOMATED IN-LINE FILTER CHANGING APPARATUS

TECHNICAL FIELD

The present invention generally relates to the filtration of media or fluids in connection with a fluid preparation, sampling, delivery, and/or testing process. More particularly, the present invention relates to the automated in-line replacement or "changing out" of used or spent filters with unused or new filters.

BACKGROUND ART

Filter elements of varying types are utilized to filter media or fluids flowing through a fluid line or circuit which forms a part of a fluid handling system. The fluid system may serve any number of processes involving one or more preparation, sampling and analytical tasks. A few examples include high-through put liquid sample assaying, high-pressure liquid chromatography, and dissolution testing. Filter elements are often installed "in-line" with such systems, and for this purpose can be housed within some type of filter unit equipped with fittings adapted for coupling and decoupling with the circuit in which fluid is moving. As with most engineered devices, it is well-known that filter elements have a limited useful life. That is, after a period of service, filters are subject to degradation, clogging and other conditions which render them no longer useful or at least cause them to impede or restrict the performance of the fluid line in which they are installed. Hence, filters must be replaced periodically, preferably according to a predetermined maintenance schedule. Depending on the process with which fluid conveying and filtering are associated, the down-time and effort required in replacing filters can be a significant criterion. It follows that any means by which the task of replacing filters can be automated, or by which the automation of filter replacement can be improved, is welcomed by the pertinent industries.

One approach to addressing the recognized problems associated with filter replacement is disclosed in U.S. Pat. No. 5,450,982 to Van Den Oever. The embodiments disclosed therein provide an automated filter changing apparatus consisting of a cylindrical filter dispensing device, a cylindrical filter clamping device, a cylindrical filter discharge device, and a means for transporting individual filters to these devices. The devices are arranged in either a linear or rotary arrangement. In the linear arrangement, a motor-powered lead screw and associated slide member are utilized to transport the filters. In the rotary arrangement, a turntable is substituted for the slide member.

According to the above-cited disclosure, a vertical stack of filters is loaded into a hollow cylinder of the filter dispenser, and the lowermost filter drops into an aperture of the transporting means when the transporting means reaches the appropriate position. The transporting means then moves the filter to a position under the clamping device. The clamping device is a pneumatic ram through which a portion of a fluid sampling line runs. The ram bears down onto the filter and establishes a connection between the filter and the fluid sampling line, so that fluid flowing through the sampling line passes through the filter and thereby becomes filtered. The filter is then transported to the discharge device, where the filter is positioned under a hollow cylinder and over a second pneumatic ram. The second pneumatic ram forces the filter upwardly into the hollow cylinder, and the filter is retained there with the aid of a retaining ring.

It is believed that there remains a need for a more practical and effective solution to providing an automated method and apparatus for replacing filters, especially filters of the type which operate in-line with a fluid circuit. There is a particular need for automating the replacement of filters which have inlet and outlet fittings extending outwardly from their housings. Such filters are often supplied in a stacked or columnar form in which each filter in the stack is connected to adjacent filters by mating the fittings of adjacent filters together. The present invention therefore provides a novel automated apparatus for changing or replacing filters, especially in-line filters, as described hereinbelow.

DISCLOSURE OF THE INVENTION

The present invention generally provides a filter changing or replacing system comprising a filter dispensing assembly and/or a filter clamping assembly. Each device includes novel attributes which permit the successful implementation of a controlled, automated filter changing process.

The filter dispensing device can be rotated, such as through the use of a motor and associated shaft. The filter dispensing device is adapted to receive filter storage units such as one or more magazines in which a plurality of filters are initially stored as a connected stack. The filter dispensing device includes a filter separating device having a stationary portion. The filter separating device operates to separate one or more stacks of filters into discrete filter units, such that individual filters are sequentially transported from the filter dispensing device, and preferably to a lateral guide track at which filter positioning devices are provided.

The filter clamping assembly is adapted to operate in combination with the filter dispensing device and to receive one or more individual filter units dispensed therefrom, and provides one or more coupling sites which can fluidly communicate with one or more fluid lines. The filter clamping assembly is powered and actuated by means such as a motor and associate lead screw. Alternating or cyclical movement of the filter clamping device decouples used filters from fittings associated with the fluid lines, and couples unused filters to those fittings.

Preferably, a filter position sensing device is provided at the clamping assembly, such as by mounting the sensing device to the lateral guide track, and a clamping position sensing device is additionally provided to monitor the position of a movable portion of the clamping assembly. In this manner, an electronic control unit can be placed in electrical communication with the position sensors and the motors to monitor and control the respective operations of both the filter dispensing device and the filter clamping device, and also coordinate the operations of those devices.

According to a first embodiment of the present invention, a filter dispensing apparatus comprises a rotary member having a longitudinal axis, and a stationary member. The stationary member includes an annular interior surface disposed in coaxial relation to the rotary member. The stationary member also includes an inlet opening, an outlet opening disposed at an axial distance from the inlet opening, and a channel formed on the interior surface. The channel runs along a generally helical path with respect to the longitudinal axis, and has a varying pitch. The pitch of the channel increases with respect to an axial length of the interior surface. The channel communicates with the inlet opening and the outlet opening.

According to a second embodiment of the present invention, a filter dispensing apparatus comprises a rotatable shaft, a filter handling device secured to the shaft and defining a first filter path, and a filter separation device. The filter separation device has an annular interior surface fixedly disposed in coaxial relation to the shaft. The filter separation device includes an entry location disposed in communication with the first filter path, an exit location disposed at an axial distance from the entry location, and a channel formed on the interior surface and defining a second filter path. The channel runs along a generally helical orientation with respect to the shaft, with a varying pitch of the channel increasing with respect to an axial length of the interior surface. The channel communicates with the entry location and the exit location.

According to a third embodiment of the present invention, a filter clamping assembly comprises an actuator device, a first arm, a second arm, a track, and a filter positioning slide. The first arm includes a first fitting disposed in movable relation to the first arm. The second arm is disposed in movable engagement with the actuator device, and includes a second fitting disposed in movable relation to the second arm. The actuator device is adapted to adjust an axial distance between the first arm and the second arm. The track is interposed between the first fitting and the second fitting, and extends along a track direction. The filter positioning slide is slidable along a slide direction transverse to the track direction.

According to a fourth embodiment of the present invention, a filter clamping assembly comprises an actuator device, a first arm, a second arm, a track, a plurality of first biasing members, and a plurality of second biasing members. The first arm includes a plurality of first fittings, with each first fitting disposed in movable relation to the first arm. The second arm is disposed in movable engagement with the actuator device and includes a plurality of second fittings, with each second fitting disposed in movable relation to the second arm. The actuator device is adapted to adjust an axial distance between the first arm and the second arm. The track is interposed between the first fittings and the second fittings. Each of the first biasing members engages a corresponding one of the first fittings for biasing the movement of that first fitting in relation to the first arm. Each of the second biasing members engages a corresponding one of the second fittings for biasing the movement of that second fitting in relation to the second arm.

According to a fifth embodiment of the present invention, an automated filter changing apparatus comprises a filter separation device and a filter clamping device. The filter separation device includes a rotary portion and a stationary portion disposed in coaxial relation to the rotary portion. The stationary portion includes an annular interior surface, an exit location and a channel formed on the interior surface. The channel runs along a generally helical path with respect to the rotary portion, with a varying pitch of the channel increasing with respect to an axial length of the interior surface. The channel communicates with the exit location. The filter clamping device includes a filter guide portion communicating with the exit location, a first fitting, and a second fitting movable with respect to the first fitting.

According to a sixth embodiment of the present invention, an automated filter changing apparatus comprises a filter dispensing device, an actuator device, a first arm, a second arm, and a track. The first arm includes a first fitting disposed in movable relation to the first arm. The second arm is disposed in movable engagement with the actuator device, and includes a second fitting disposed in movable relation to the second arm. The actuator device is adapted to adjust an axial distance between the first arm and the second arm. The track communicates with the filter dispensing device and is interposed between the first fitting and the second fitting.

According to a seventh embodiment of the present invention, an automated filter changing apparatus comprises a filter dispensing device, a filter positioning track, and a filter coupling device. The filter positioning track communicates with the filter dispensing device and defines a plurality of laterally spaced filter coupling sites. The filter coupling device includes a plurality of first fluid fittings and a plurality of second fluid fittings. Each first fluid fitting is disposed over one of the coupling sites, and each second fluid fitting is disposed under one of the coupling sites.

According to an eighth embodiment of the present invention, an automated filter changing apparatus comprises a filter dispensing device, a filter positioning track, a filter clamping device, a first position sensing device, a second position sensing device, and an electronic control unit communicating with the first and second position sensing devices. The filter positioning track is disposed in operative communication with the filter dispensing device and defines a plurality of laterally spaced filter coupling sites. The filter clamping device includes a movable member and a plurality of generally oppositely oriented first and second fluid fittings. Each first fluid fitting is disposed over one of the coupling sites, and each second fluid fitting is disposed under one of the coupling sites. The first position sensing device is disposed in operative alignment with one of the coupling sites. The second position sensing device is disposed in operative alignment with the movable member of the filter clamping device.

According to a ninth embodiment of the present invention, an apparatus for replacing a filter in a fluid line comprises a rotary filter handling device, a stationary filter handling device, a filter guiding device, and a filter clamping device. The rotary filter handling device defines a generally downward first filter path. The stationary filter handling device defines a generally helical second filter path which communicates with the first filter path. The filter guiding device defines a third filter path. The third filter path communicates with the second filter path and is oriented in a generally transverse relation to the first filter path. The filter clamping device communicates with a fluid line, and is adapted for releasable engagement with a filter disposed in the filter guiding device.

According to a tenth embodiment of the present invention, an apparatus for replacing a filter in a fluid line comprises a filter storage device, a filter clamping device, and means for transposing a plurality of filters from a stacked arrangement in the filter storage device to a sequential, lateral arrangement in the filter clamping device.

According to an eleventh embodiment of the present invention, an apparatus for connecting a plurality of filters to a plurality of corresponding fluid lines comprises a filter storage device, a filter clamping device, filter conveying means, and clamping force distributing means. The filter clamping device includes a plurality of pairs of inlet and outlet fittings, with each pair of inlet and outlet fittings are adapted for communication with a fluid line. The filter clamping device is adapted to impart a total clamping force to a plurality of filters received in the filter clamping device to connect each filter, under influence of a portion of the total clamping force, in fluid communication with a corresponding one of the pairs of inlet and outlet fittings. The filter conveying means conveys the plurality of filters from the filter storage device to the filter clamping device. The clamping force distributing means distributes the total clamping force to the plurality of filters to reduce variations among the portions of the total clamping force imparted to each filter by the filter clamping device.

According to a twelfth embodiment of the present invention, an apparatus for connecting a filter to a fluid line comprises a filter storage device, a filter clamping device, filter conveying means, and filter positioning means, The filter clamping device includes an inlet fitting and an outlet fitting, which are adapted for communication with a fluid line. The filter conveying means conveys a filter having first and second fittings from the filter storage device to the filter clamping device. The filter positioning means aligns the first fitting of the filter with the inlet fitting of the filter clamping device, and the second fitting of the filter with the outlet fitting of the filter clamping device.

It is therefore an object of the present invention to provide an apparatus for dispensing one or more filters to a device which subsequently couples the filter to a fluid line or fluid circuit.

It is another object of the present invention to provide an apparatus for dispensing a plurality of filters initially provided in a stacked form wherein the fittings of each filter in the stack are typically mated to the fittings of adjacently situated filters, such that the filter stack encounters a separating device which separates each filter from the other filters, and with the result that each filter is dispensed individually with respect to the other filters.

It is yet another object of the present invention to provide an automated apparatus for replacing one or more existing filters operating within a fluid line with one or more unused filters by dispensing individual, unused filters to a filter clamping device, decoupling the existing filters from the fluid line, positioning the unused filters at appropriate coupling sites of the fluid line, and coupling the unused filters to the fluid line at the coupling sites.

It is still another object of the present invention to provide a filter changing apparatus which coordinates the operations of a filter dispensing device with a filter clamping device, in part by counting the number of individual filters being loaded into the clamping device and by determining when the clamping device has reached an open state at which used filters can be replaced with new filters.

It is a further object of the present invention to provide a filter clamping apparatus which permits used filters to be decoupled from a fluid line for subsequent replacement with unused filters, wherein the filter clamping apparatus can evenly distribute the clamping force needed for connecting each filter with inlet and outlet fittings of the fluid line corresponding to that filter.

It is an additional object of the present invention to provide a filter changing apparatus which includes a filter positioning device that ensures that filters transported by the filter changing apparatus are brought into proper alignment with a filter clamping device.

Some of the objects of the invention having been stated hereinabove, other objects will become evident as the description proceeds when taken in connection with the accompanying drawings as best described hereinbelow.

BRIEF DESCRIPTION OF THE DRAWINGS

FIG. 1 is a perspective view of a filter changing apparatus provided in assembled form according to the present invention;

DETAILED DESCRIPTION OF THE INVENTION

Figure 2B:
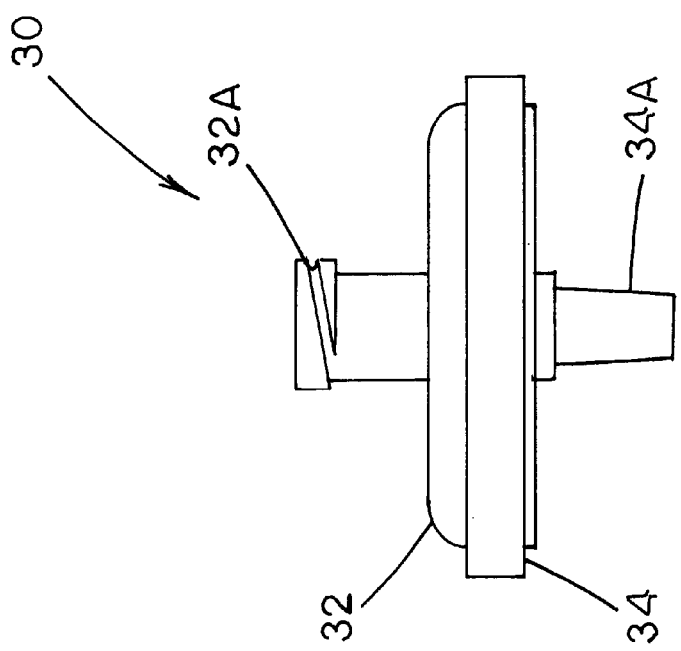
FIGS. 2A and 2B are exploded and assembled side elevation views, respectively, of a filter unit suitable for use in conjunction with the filter changing apparatus illustrated in FIG. 1.

Referring now to FIG. 1, an automated in-line filter changing apparatus generally designated 10 is illustrated in assembled form. By way of example, filter changing apparatus 10 has a structural framework generally including an upper deck 12 and a lower deck 14. Upper deck 12 is supported above lower deck 14 by one or more spacer members 16. Broadly stated, filter changing apparatus 10 includes a filter unit storage, separation and dispensing assembly generally designated 50 (hereinafter referred to as "filter separation assembly 50"), a filter unit clamping assembly generally designated 100, and an electronic control unit generally designated 200. In the embodiment illustrated in FIG. 1, filter separation assembly 50 and filter clamping assembly 100 are supported on upper deck 12. Filter changing apparatus 10 also includes a filter unit positioning track, generally designated 130, mounted on upper deck 12. A series of one or more fluid line fittings 18 are installed in a bracket 21 mounted to lower deck 14, and are adapted to be coupled with the conduits of a fluid circuit (not shown). Filter changing apparatus 10 further includes a filter unit position sensor generally designated 23 and a filter unit clamping assembly position sensor generally designated 25, the details and functions of which are described hereinbelow. Preferably, many of the various components of filter changing apparatus 10 illustrated in FIG. 1, with the possible exception of the upper portions of filter separation assembly 50, are contained within a housing structure with a removable top cover which are not shown for purposes of clarity.

Figure 2A:
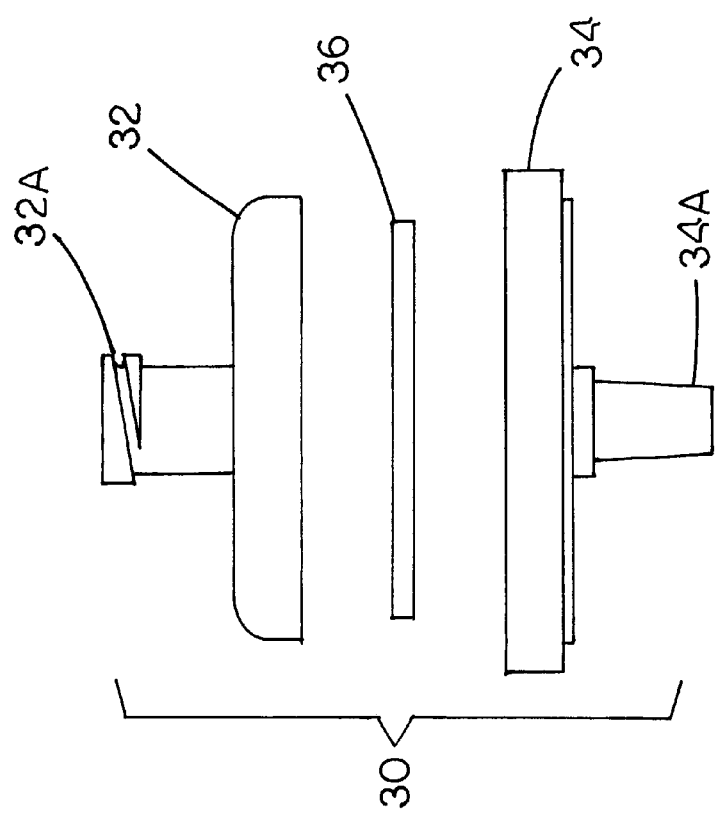

In a preferred implementation of the present invention, filter separation assembly 50, filter clamping assembly 100 and electronic control unit 200 operate in conjunction with each other to automate the replacement of "in-line" type filter units. Such filter units can be those typically employed in a fluid sampling or fluid delivery system. Suitable filter units are manufactured by Millipore Inc. and are available from VanKel Technology Group as Part No. 17-4220. The respective exploded and assembled views of FIGS. 2A and 2B illustrate an example of a suitable filter unit, generally designated 30. Filter unit 30 has Luer-style fittings which, when fitted to flexible conduits or tubing, require only an axial load in order to establish an adequate seal. Exemplary filter unit 30 includes an upper shell portion 32 with a hollow female fitting 32A, a lower shell portion 34 with a hollow male fitting 34A, and a filter element 36 housed therebetween. The implementation of filter changing apparatus 10 illustrated in FIG. 1 is useful in many chemistry-related processes wherein filter units 30 are prone to clogging, chemical carry-over or other conditions requiring filter replacement, and wherein it is advantageous that such replacements be controlled and/or timed with relationship to some other device or instrument.

Referring to FIGS. 3–7, various details of filter separation assembly 50 and related components are illustrated. The exemplary assembly 50 as illustrated herein performs the functions of storing a supply of unused filter units 30, separating individual filter units 30, and delivering each individual filter unit 30 to filter clamping assembly 100. In the preferred embodiment, these functions are integrated into a single assembly which has both rotating and stationary portions, but it will be understood that structurally distinct storage, separation and dispensing subassemblies could be implemented in accordance with the present invention.

Figure 3:
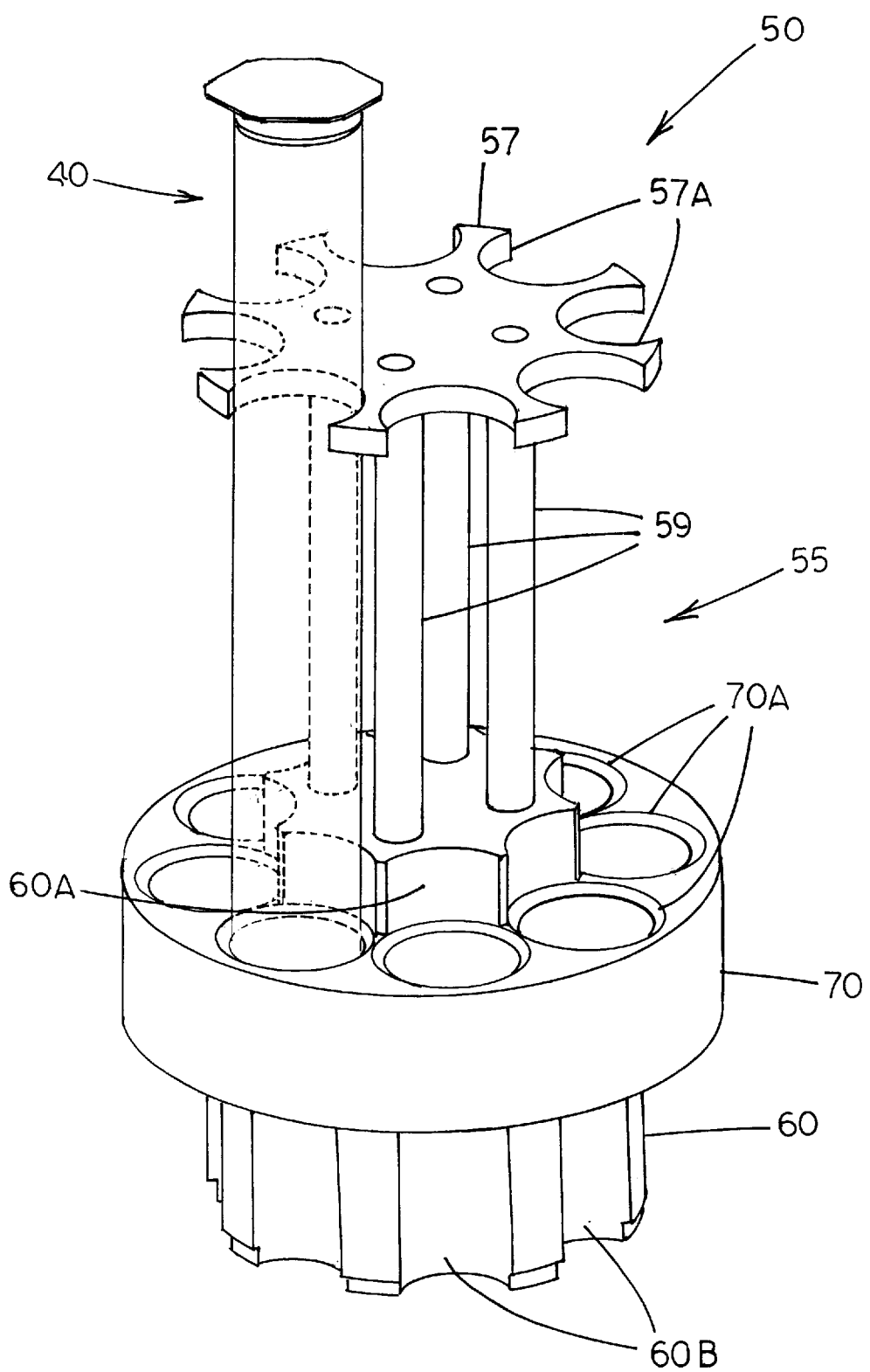
FIG. 3 is a perspective view of a rotatable portion of a filter unit separation assembly forming a part of the filter changing apparatus illustrated in FIG. 1.
Figure 4:
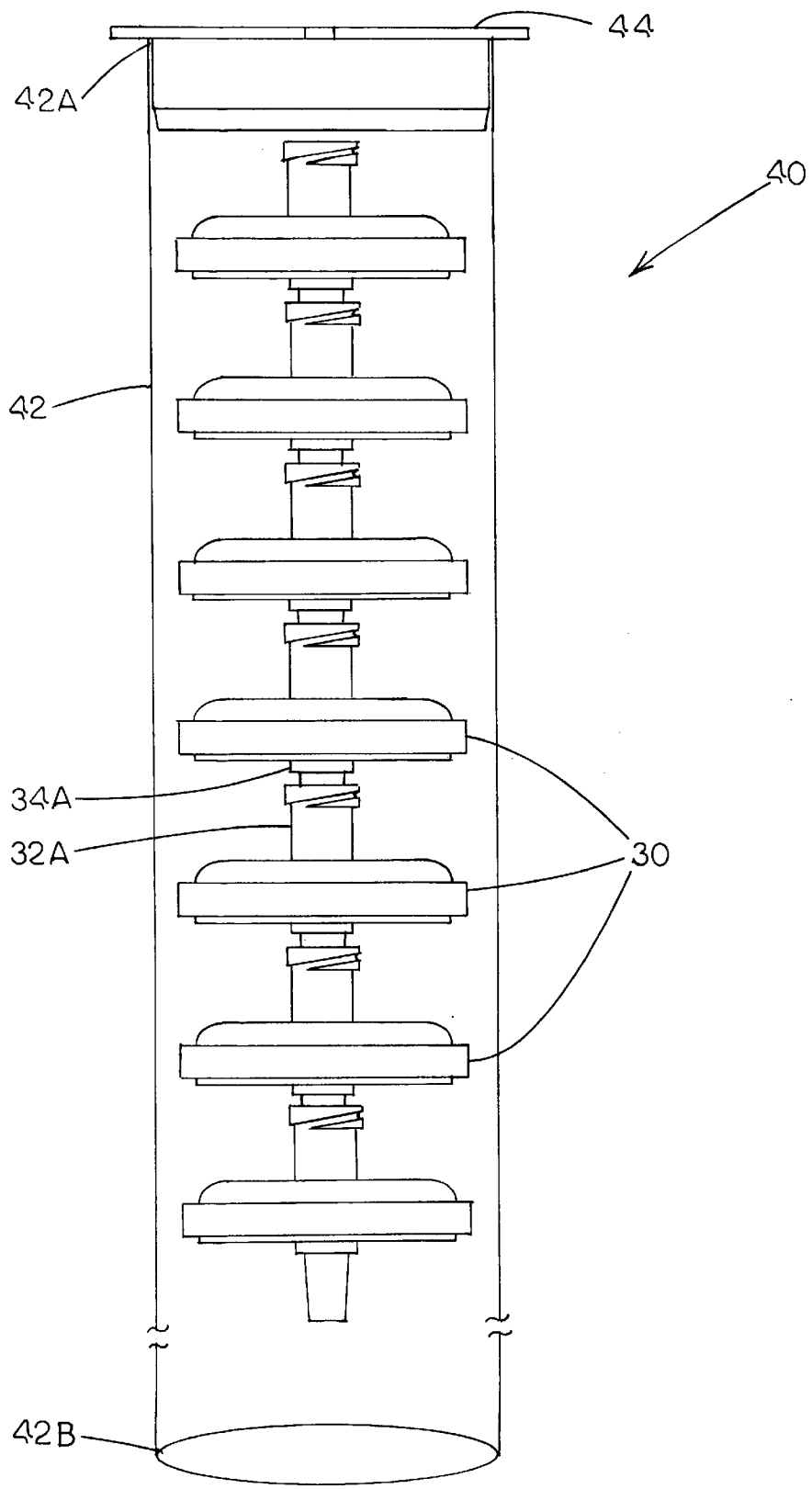
FIG. 4 is a side elevation view of a filter unit storage magazine, with a stack of connected filter units contained therein, adapted for use in conjunction with the filter changing apparatus illustrated in FIG. 1.

Referring specifically to FIG. 3, filter separation assembly 50 includes a filter unit magazine holding and support device in the form of a filter unit magazine carrousel generally designated 55, and a rotor 60 attached thereto. Referring to FIG. 4, magazine carrousel 55 is adapted to hold and support one or more filter unit magazines, generally designated 40, for example eight magazines 40, which are preferably provided in a tube-like or cylindrical form. As shown in FIG. 4, filter unit magazine 40 includes a magazine wall 42 and open upper and lower ends 42A and 42B, respectively. Magazine wall 42 is preferably constructed from a transparent material. Filter unit magazine 40 is adapted to receive and store a plurality of filter units such as filter units 30 in a stacked arrangement, wherein each filter unit 30 is connected or mated to at least one other adjacent filter unit 30 by inserting male fitting 34A of one or more filter units 30 into female fitting 32A of an adjacent filter unit 30. In one exemplary embodiment, each magazine 40 is adapted to store a stack or column of 25 filter units 30 such that when eight magazines 40 are employed, a total of 200 unused filter units 30 can be loaded into filter separation assembly 50. If desired, magazines 40 can be lengthened in order to hold an additional number of filter units 30. An end cap 44 can be attached to upper end 42A of each magazine 40 to close off upper end 42A. An additional end cap (not shown) can be attached to lower end 42B to fully confine a stack of filter units 30 within magazine 40 when magazine 40 is not loaded into magazine carrousel 55.

Referring back to FIG. 3, magazine carrousel 55 includes an upper rack 57 situated at a distance from rotor 60 by means of one or more elongate spacer members 59. Upper rack 57 defines recessed sections 57A shaped to laterally support or at least accommodate the profile of each magazine 40 installed in magazine carrousel 55. One or more magazines 40 are installed in filter separation assembly 50 by inserting their respective lower ends 42B into bores 70A of a barrel portion 70. Depending on the particular design implemented, barrel portion 70 can be considered as forming a part of either magazine carrousel 55 or rotor 60. As further shown in FIG. 3, rotor 60 includes upper recessed sections 60A disposed above barrel portion 70 and lower recessed sections 60B disposed below barrel portion 70. Upper recessed sections 60A are shaped to accommodate the shape of magazines 40, and lower recessed sections 60B are shaped to accommodate the shape of filter units 30 traveling out of barrel portion 70, as described in more detail hereinbelow.

Referring to FIG. 1 and the cutaway view of FIG. 5, filter separation assembly 50 also includes an internally threaded, annular base block or collar 80 mounted on upper deck 12 below barrel portion 70, and circumscribing at least a lower portion of rotor 60. Magazine carrousel 55 and rotor 60 rotate together about the axis of a rotor shaft 65 in the counterclockwise direction indicated by arrow A in FIG. 5, while base block 80 remains stationary. Referring back to FIG. 1, rotor shaft 65 is driven by a stepper motor 67 housed between upper and lower decks 12 and 14 of filter unit changing apparatus 10. Motor 67 is supported by a bracket 67A, and appropriate gearing or transmission means (not specifically shown) situated underneath upper deck 12 provide mechanical coupling and rotational speed adjustment between motor 67 and rotor shaft 65.

Figure 6:
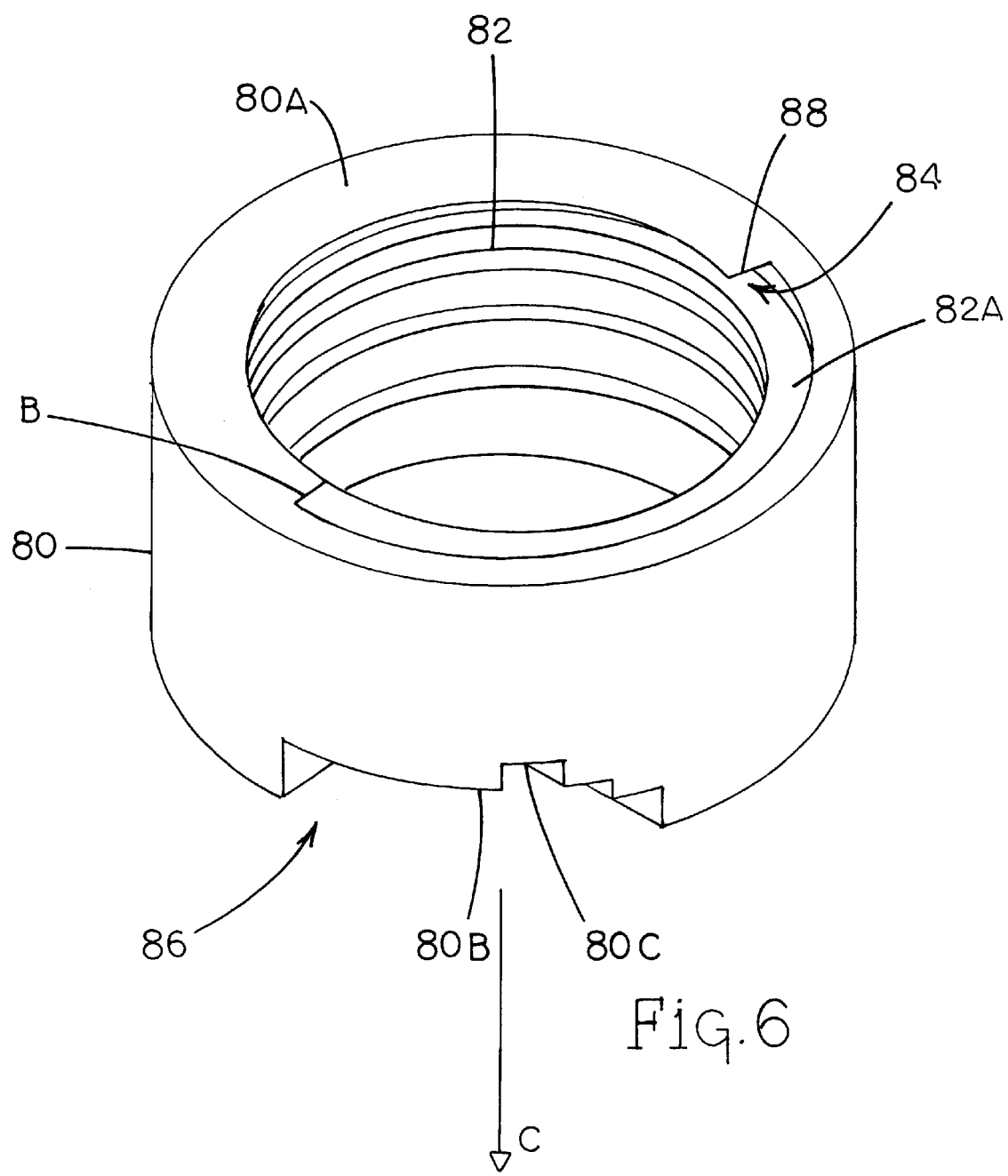
FIG. 6 is a perspective view of the stationary portion of the filter unit separation assembly illustrating an internal threaded or grooved design.
Figure 7:
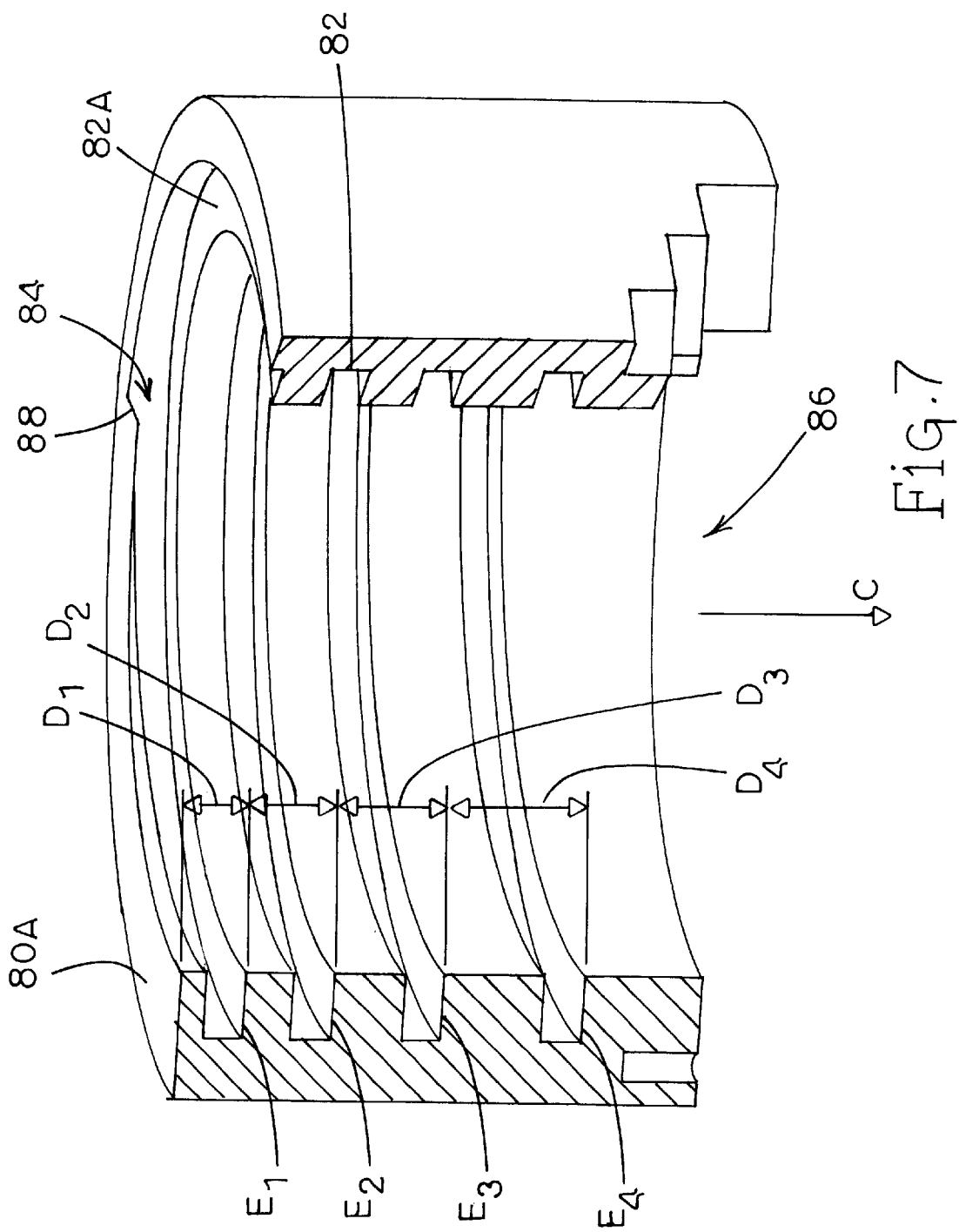
FIG. 7 is a perspective partial cutaway view of the stationary portion illustrated in FIG. 6.

Referring to FIGS. 6 and 7, base block 80 includes a continuous, helical or spiral groove or channel 82 oriented along a generally helical or spiral path leading from a starting point B near the top of base block 80 to a terminal point (not specifically shown) near the bottom of base block 80. For a purpose to be described hereinbelow, helical groove 82 is characterized by an increasing pitch in the axial direction represented by arrow C. The increasing pitch is illustrated in FIG. 7 by observing the increasing distances $D_1$, $D_2$, $D_3$ and $D_4$ between a lower surface 82A of helical groove 82 at axially spaced elevation points $E_1$, $E_2$, $E_3$ and $E_4$ shown along the cross-section of base block 80. To provide an entry point for individual filter units 30 into helical groove 82 and into base block 80 and an exit point therefrom, base block 80 defines a filter unit entry location generally designated 84 and a filter unit exit location generally designated 86, respectively. Entry location 84 is generally defined between point B and a lip 88, which lip 88 is defined at a top surface 80A of base block 80 and protrudes radially inwardly toward the axis of rotor shaft 65. Exit location 86 is defined by a number of surfaces or edges such as surfaces 80B and 80C designed in part to accommodate the profile of filter units 30 exiting therefrom.

Figure 8:
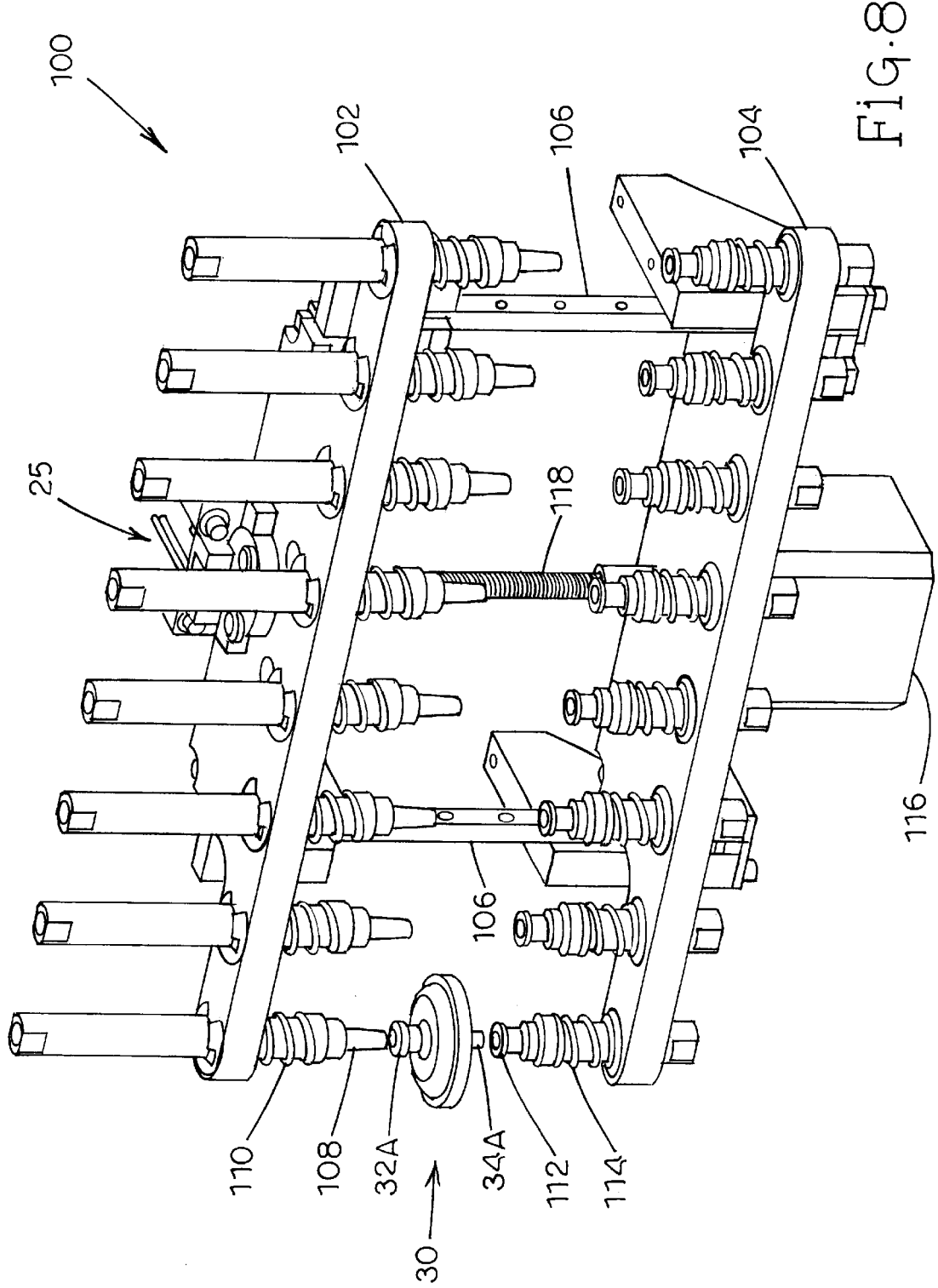
FIG. 8 is a perspective view of a filter unit clamping assembly forming a part of the filter changing apparatus illustrated in FIG. 1.
Figure 9:
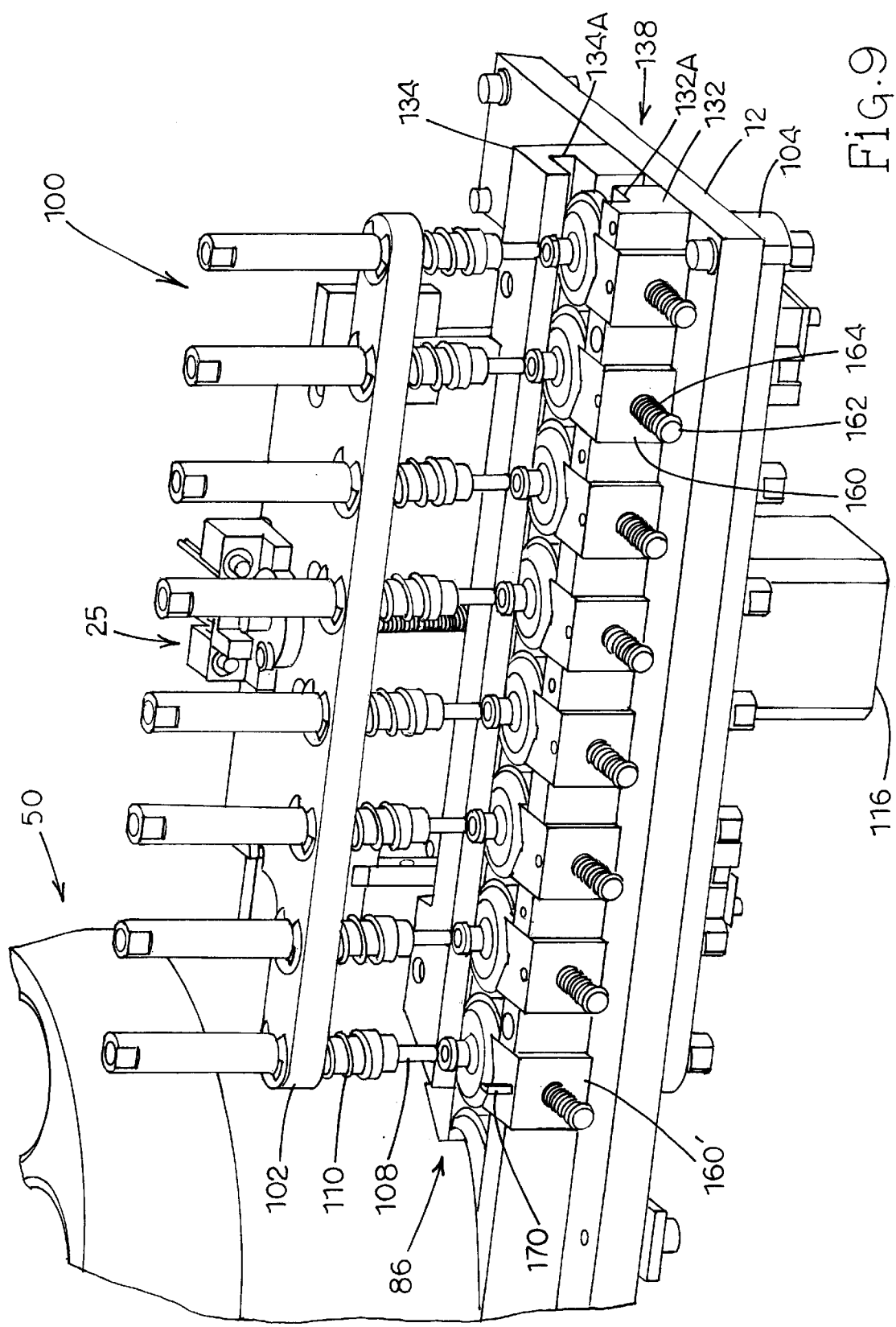
FIG. 9 is a detailed perspective view of a section of the filter changing apparatus illustrated in FIG. 1 wherein the filter unit clamping assembly illustrated in FIG. 8 has been installed in the filter changing apparatus.
Figure 10:
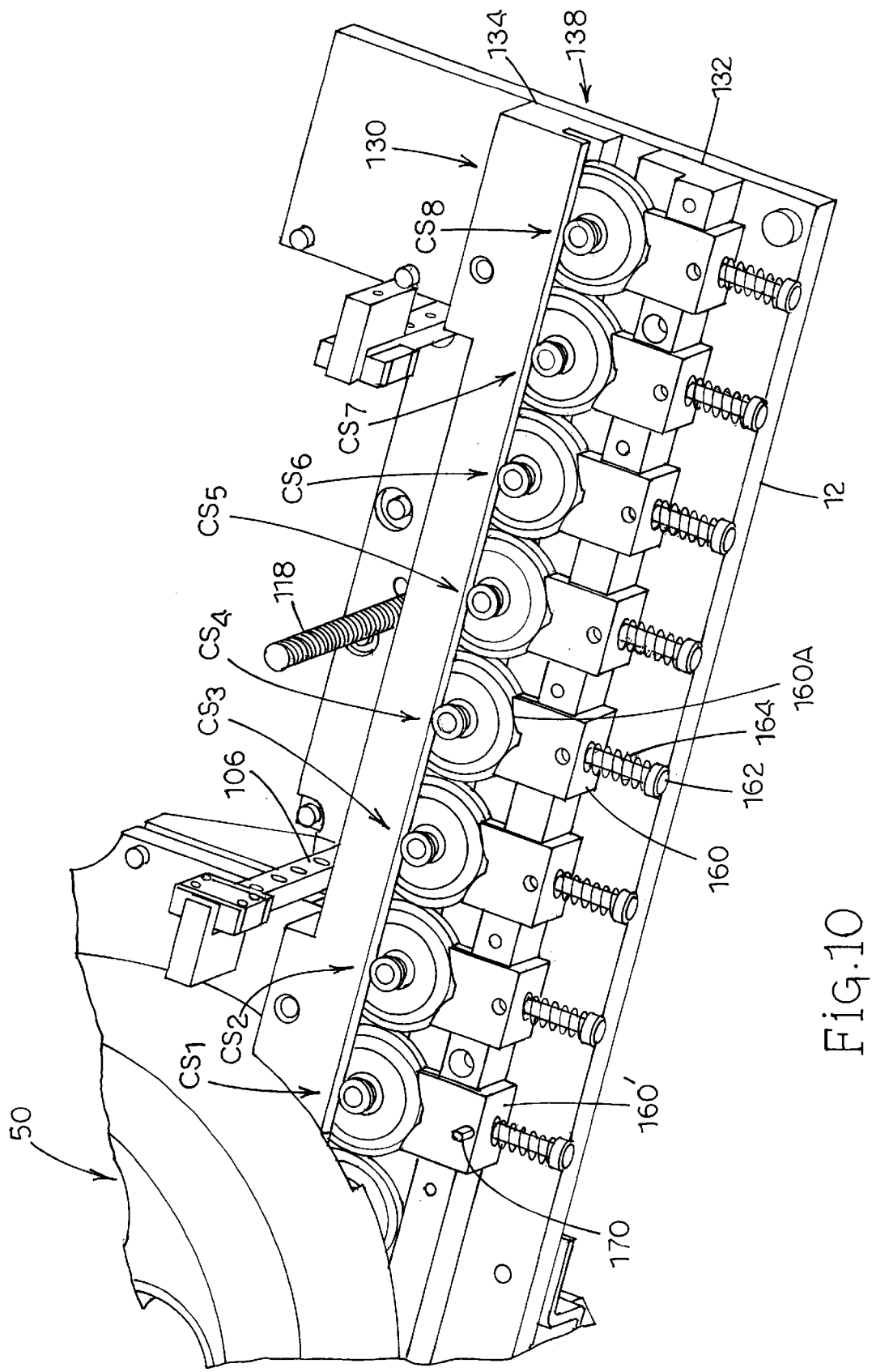
FIG. 10 is a detailed perspective view of a section of the filter changing apparatus illustrated in FIG. 1, wherein a portion of the filter unit clamping assembly has been removed to highlight a lateral track forming a part of the filter changing apparatus and components utilized to position filter units in the lateral track.

Referring to FIGS. 8–10, filter unit clamping assembly 100 and related components of filter changing apparatus 10 are illustrated in more detail. As will become evident hereinbelow, the primary function of filter clamping assembly 100 is to couple one or more new filter units 30 dispensed from filter separation assembly 50 to a fluid circuit communicating with filter clamping assembly 100 and thereby establish one or more flow paths therethrough, as well as to decouple used filter units 30 from the fluid circuit once such filter units 30 have been in service for a predetermined period of time or number of cycles. For the purpose of description, filter clamping assembly 100 defines one or more fluid coupling sites generally designated $CS_1$–$CS_8$, respectively (see FIG. 10). The fluid circuit referenced herein can be part of any number of different types of processes, involving various apparatuses situated both upstream and downstream of filter changing apparatus 10, such as fluid pumps, dissolution testing stations, liquid chromatography devices, and the like.

Filter unit clamping assembly 100 includes an upper arm 102, a lower arm 104, and one or more vertical rails 106 along which upper arm 102 slides with respect to lower arm 104. In the exemplary embodiment illustrated in FIGS. 1 and 9, lower arm 104 is secured to the underside of upper deck 12 of filter changing apparatus 10. One or more upper male fittings 108 are movably supported through the thickness of upper arm 102 and are biased by load springs 110. Likewise, one or more corresponding lower female fittings 112 are movably supported through the thickness of lower arm 104 in coaxial alignment with upper fittings 108, and are also biased by load springs 114. There is accordingly a pair of upper and lower fittings 108 and 112 for each coupling site $CS_1$–$CS_8$, with upper fittings 108 situated generally above lateral track 130 and lower fittings 112 situated generally below later track 130. The displacement of upper arm 102 with respect to lower arm 104 is driven by a stepper motor 116, which is mounted between upper and lower decks 12 and 14 of filter changing apparatus 10 as shown in FIG. 1, and an associated lead screw 118.

The illustrated driving means is preferred for its strength, speed, reliability, controllability and quietness, and because it does not require continuous power in order to maintain clamping force. It will be understood, however, that other known means such as pneumatic or solenoid-type actuating devices could be provided in the place of stepper motor 116 and lead screw 118 for producing a clamping action with the required clamping force.

Load springs 110 and 114 ensure that an excessive clamping force exerted by clamping assembly 100 does not damage fittings 32A and 34A of filter units 30 or crush filter units 30 and, when more than one filter unit 30 is placed in use in filter clamping assembly 100, that the clamping force is evenly distributed among the several filter units 30 residing in lateral track 130. That is, because all upper fittings 108 are supported in a single upperarm 102 in the exemplary embodiment, and all lower fittings 112 are supported in a single lower arm 104, a fraction of the total clamping force developed by clamping assembly 100 is transferred to each filter unit 30 residing at the coupling sites $CS_1$–$CS_8$. The design of clamping assembly 100 according to the present invention, however, ensures that this total clamping force is substantially evenly distributed to each filter unit 30, such that the fractional clamping force imparted to one filter unit 30 is substantially equal to the fractional clamping forces respectively imparted to the other filter units 30.

Referring to FIGS. 1 and 9–11, filter unit positioning track 130 and associated filter unit position sensor 23 are illustrated. Track 130 is disposed in a lateral orientation with respect to filter separation assembly 50. Preferably, track 130, upper fittings 108 and lower fittings 112 are further arranged in a linear orientation, although it will be understood that a curved orientation could be employed without affecting the sequential, side-by-side loading of filter units 30 into filter clamping assembly 100. Track 130 includes a front guide rail 132 and a rear guide rail 134 which face each other and are mounted on upper deck 12 of filter changing apparatus 10. Front and rear guide rails 132 and 134 each have opposing channels or grooves 132A and 134A which, in conjunction with the spacing between front and rear guide rails 132 and 134, provide an open track volume with a cross-section shaped to accommodate the cross-sectional profile of filter units 30. In this manner, filter units 30 can slide laterally through track 130 in a guided manner with their female fittings 32A oriented upwardly. In addition, at each coupling site $CS_1$–$CS_8$, respective female fittings 32A of filter units 30 can become aligned with corresponding male fittings 108 of filter clamping assembly 108, and respective male fittings 34A of filter units 30 can become aligned with corresponding female fittings 112 of filter clamping assembly 100. The open track volume begins at an inlet end (not specifically shown) of lateral track 130 which directly or indirectly communicates with exit location 86 of base block 80, and terminates at a discharge end, generally designated 138. A waste receptacle (not shown) can be provided to receive filter units 30 expelled from discharge end 138.

Figure 11:
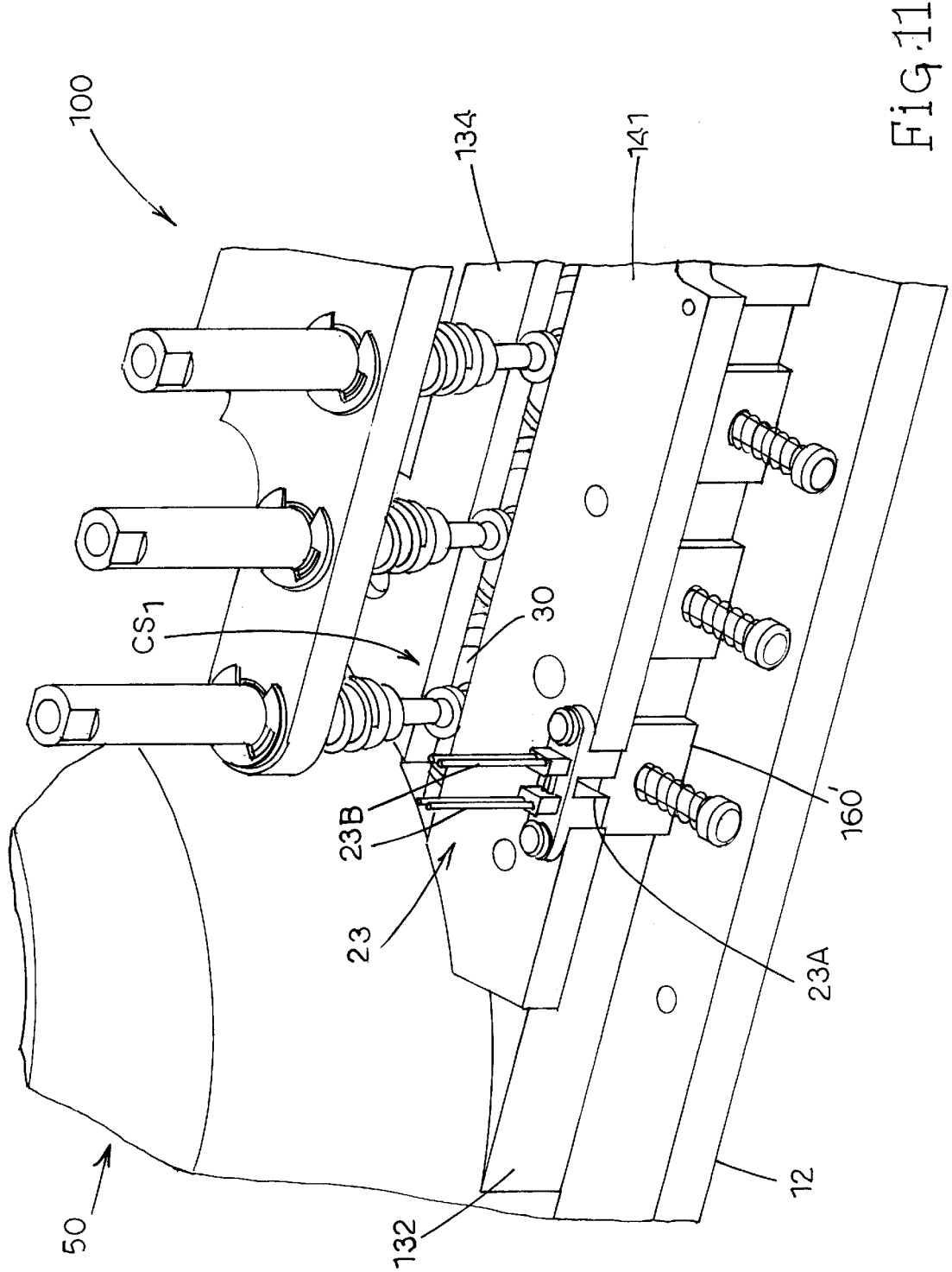
FIG. 11 is a detailed perspective view of a section of the filter changing apparatus illustrated in FIG. 1, wherein a sensing device has been provided in accordance with the present invention.

Preferably, front guide rail 132 includes a removable top portion 141 (see FIGS. 1 and 11). With top portion 141 removed as shown in FIGS. 9 and 10, it is seen that front guide rail 132 has a plurality of recesses adapted to receive a plurality of filter unit retainer elements or positioning slides 160. Preferably, at least one filter positioning slide 160 exists for each coupling site $CS_1$–$CS_8$. Positioning slides 160 move within the recesses of front guide rail 132 along a direction transverse to the direction of lateral track 130, and are guided along respective posts 162. Each positioning slide 160 has a generally indented or recessed inner edge 160A, and includes a spring 164 mounted about its associated post 162 to bias slide 160 inwardly toward lateral track 130. By this configuration, each positioning slide 160 assists in aligning fittings 32A and 34A of each filter unit 30 with correspondingly situated fittings 108 and 112 of filter clamping assembly 100, such that one or more filter units 30 can be serially or sequentially positioned at coupling sites $CS_1$–$CS_8$ in an indexing fashion.

As best shown in FIG. 11, at least one filter unit positioning sensor 23 is mounted in a cut-out section of top portion 141 of front guide rail 132 over first positioning slide (herein specifically designated 160') and proximate to first coupling site $CS_1$ of filter clamping assembly 100—that is the first coupling site encountered by filter units 30 as they exit from filter separation assembly 50 into lateral track 130. Preferably , filter unit positioning sensor 23 is an LED device , and includes a structural gap 23A across which a light beam is directed and electrically conductive leads 23B communicating through conduits (not shown) with electronic control unit 200. Filter unit positioning sensor 23 functions in cooperation with a home sensor flag 170 to detect the arrival and proper alignment of a filter unit 30 at first coupling site $CS_1$. Home sensor flag 170 is provided essentially in the form of an elongate structural member as shown in FIGS. 9 and 10, and protrudes upwardly from first positioning slide 160'.

Home sensor flag 170 moves with first positioning slide 160'. Thus , as a filter unit 30 moves along lateral track 130 toward the position at first coupling site $CS_1$, filter unit 30 initially pushes first positioning slide 160' outwardly from lateral track 130, thereby building up stored potential energy in associated spring 164. As filter unit 30 continues to approach first coupling site $CS_1$, indented edge 160A of first positioning slide 160' permits spring 164 to relax. That is , the combination of spring 164 and indented edge 160A of first positioning slide 160' coact to urge filter unit 30 into the properly aligned position at first coupling site $CS_1$, such that fittings 32A and 34A of filter unit 30 are aligned with corresponding fittings 108 and 112 of filter clamping assembly 100. The displacement of first positioning slide 160' with respect to lateral track 130 and front guide rail 132 causes home sensor flag 170 to break the light beam produced by filter unit position sensor 23 across its gap 23A, so that filter unit position sensor 23 detects when filter unit 30 has reached the properly aligned "home" position at first coupling site $CS_1$. When more than one filter unit 30 is to be employed along lateral track 130, filter unit position sensor 23 and home sensor flag 170 are also utilized to count the number of filter units 30 that have been advanced along lateral track 130 into alignment with coupling sites $CS_1$–$CS_8$. Hence, after a predetermined number of filter units 30 have been positioned in filter clamping assembly 100, an appropriate signal can be generated by electronic control unit 200 to cause filter separation assembly 50 to cease rotation and thus to cease advancement of filter units 30 into lateral track 130.

Figure 12:
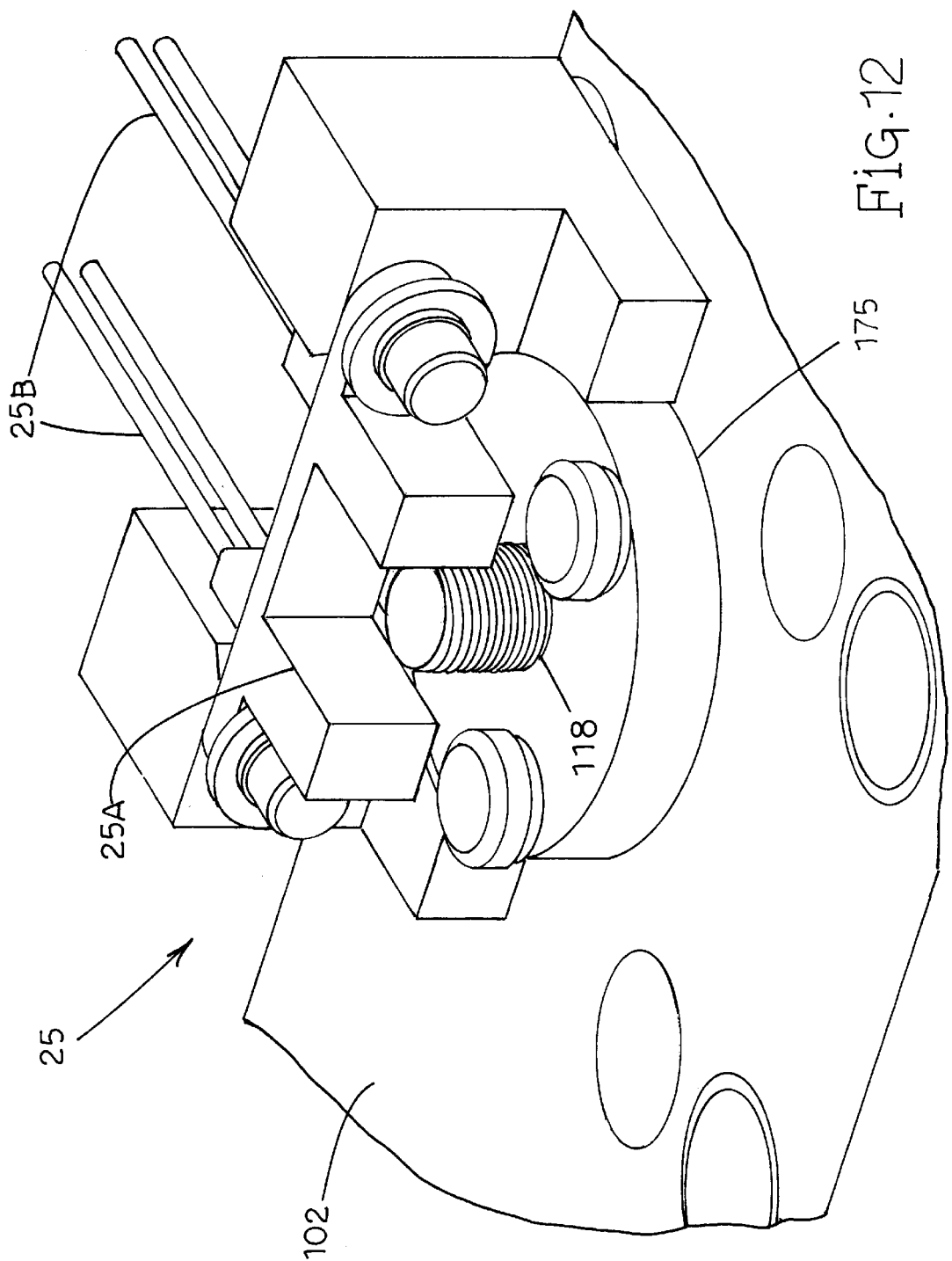
FIG. 12 is a detailed perspective view of a section of the filter changing apparatus illustrated in FIG. 1, wherein another sensing device has been provided in accordance with the present invention.

Referring to FIG. 12, clamping assembly position sensor 25 is mounted to upper arm 102 of filter clamping assembly 100 and straddles a threaded lead screw nut 175 through which lead screw 118 is rotatably supported. Preferably, clamping assembly position sensor 25 is of the same design as filter unit position sensor 23, and thus includes a structural gap 25A across which a light beam is directed and electrically conductive leads 25B communicating through conduits (not shown) with electronic control unit 200. Lead screw 118 serves as the home sensor flag for clamping assembly position sensor 25. When upper arm 102 reaches its uppermost position with respect to lower arm 104, the topmost surface of lead screw is disposed below gap 25A, at which point the light beam is unbroken and clamping assembly position sensor 25 detects that upper arm 102 is "home."

Figure 13:
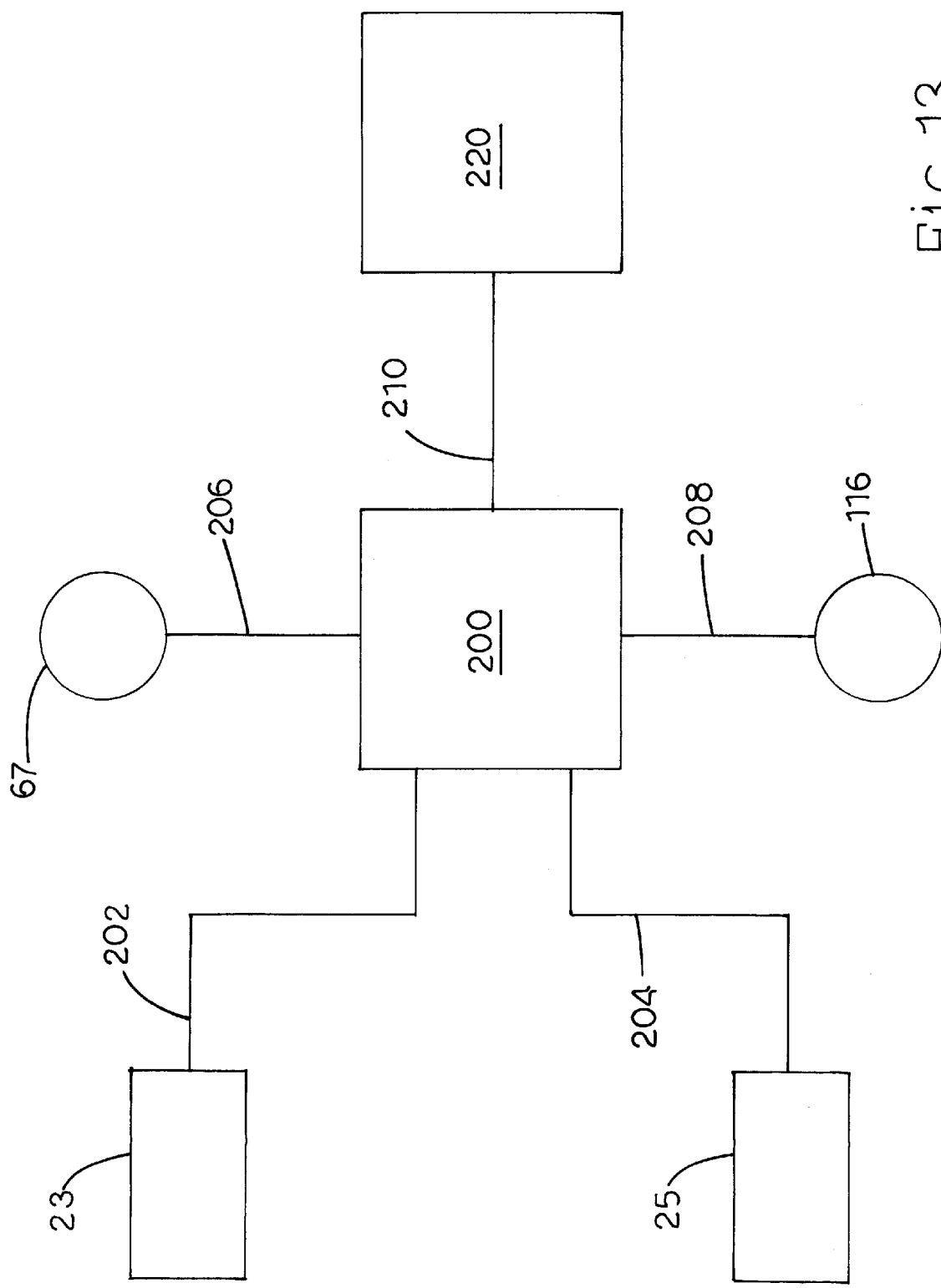
FIG. 13 is a simplified schematic diagram of an electronic control circuit employed in conjunction with the present invention.

Referring to FIG. 13, a simplified schematic diagram of electronic control unit 200 and its associated circuit are illustrated. The primary function of electronic control unit 200 is to control and coordinate the relative motions of filter separation assembly 50 and clamping assembly 100, according to principles known to those skilled in the art. Electronic control unit 200 can be disposed in a suitable location such as being integrated in filter changing apparatus 10 as shown in FIG. 1, although electronic control unit 200 could be situated in a remote location with respect to filter changing apparatus 10. Electronic control unit 200 is adapted to receive signals from filter unit position sensor 23 over line 202 and from clamping assembly position sensor 25 over line 204. Electronic control unit 200 is also adapted to send signals to motor 67 associated with filter separation assembly 50 over line 206 and to motor 116 associated with filter clamping assembly 100 over line 208. Electronic control unit 200 can also be adapted to receive computer coded commands, and preferably both RS232 and RS485 serial commands, from a secondary control unit 220 over line 210. Alternately, electronic control unit 200 itself can be adapted to both process inputted commands and condition signals. Secondary control unit 220 can be provided in the form of a CPU-based device, such as a remote computer terminal, or could represent an electronic control device which is part of an additional apparatus situated upstream or downstream of the fluid lines communicating with filter changing apparatus 10.

In operation, filter changing apparatus 10 is configured to handle a predetermined number of magazines 40 (e.g., one to eight magazines 40), each containing a stack of filter units 30. One or more magazines 40 are then loaded into a bore or bores 70A of barrel portion 70 of filter separation assembly 50. At this point, depending on the rotary position of rotor 60 and magazines 40 relative to base block 80, the lowermost filter unit 30 of one of the stacks will have come to rest either on top surface 80A of base block 80 or directly on the initial section of base block groove 82 within entry location 84 (see FIGS. 6 and 7). During normal use, a predetermined number of used filter units 30 are operatively positioned along lateral track 130 at coupling sites $CS_1$–$CS_8$ and clamping assembly 100 is disposed in its fully closed or clamped position. Accordingly, male and female fittings 34A and 32A of each used filter unit 30 are mated to corresponding female and male fittings 112 and 108 of clamping assembly 100, the fluid circuit in which filter changing apparatus 10 is operating is closed, and the fluid flow paths are thus operative.

If it is determined (either manually or according to a programmed schedule) that working filter units 30 should be replaced with new filter units 30, electronic control unit 200 either generates a command to change out filter units 30 or receives the command from secondary control unit 220. Following this command for filter replacement, electronic control unit 200 sends an appropriate control signal to activate clamping assembly motor 116. Motor 116 powers lead screw 118 to cause upper arm 102 of clamping assembly 100 to travel upwardly, thus opening clamping assembly 100, decoupling filter units 30 residing in lateral track 130 from fittings 108 and 112 of clamping assembly 100, and consequently switching the fluid circuit into an open-circuit state. When upper arm 102 reaches its uppermost "home" position shown in FIG. 12, this event is detected by clamping assembly position sensor 25 as described hereinabove, and clamping assembly position sensor 25 sends a transduced signal to electronic control unit 200. In response, electronic control unit 200 sends an appropriate control signal to activate filter separation assembly motor 67, which causes rotor 60 to turn filter separation assembly 50 in a counterclockwise orientation about the axis of rotor shaft 65.

As rotor 60 rotates magazine carrousel 55 of filter separation assembly 50, lowermost filter unit 30 of at least one magazine 40 gravitates from barrel portion 70 through entry location 84 into base block groove 82 and is guided by one of lower recesses 60B of rotor 60. As generally illustrated in FIG. 5, filter units 30 of other magazines 40 begin to follow the same path. Protruding lip 88 of base block 80 ensures that lowermost filter unit 30 begins to properly travel along the curved path of groove 82, such that upper shell portion 32 of lowermost filter unit passes underneath lip 88. As rotor 60 continues to turn, the pitch of groove 82 increases as described hereinabove with reference to FIG. 7. As a result, the rotation of rotor 60 with respect to groove 82 urges the spacing to increase between lowermost filter unit 30 and the filter unit connected to lowermost filter unit 30. At some point within base block 80, lowermost filter unit 30 becomes completely disconnected from its associated filter stack. Continued rotation causes separated filter unit 30 to exit base block 80 (and thus filter separation assembly 50) through exit location 86 and enter lateral track 130.

Figure 5:
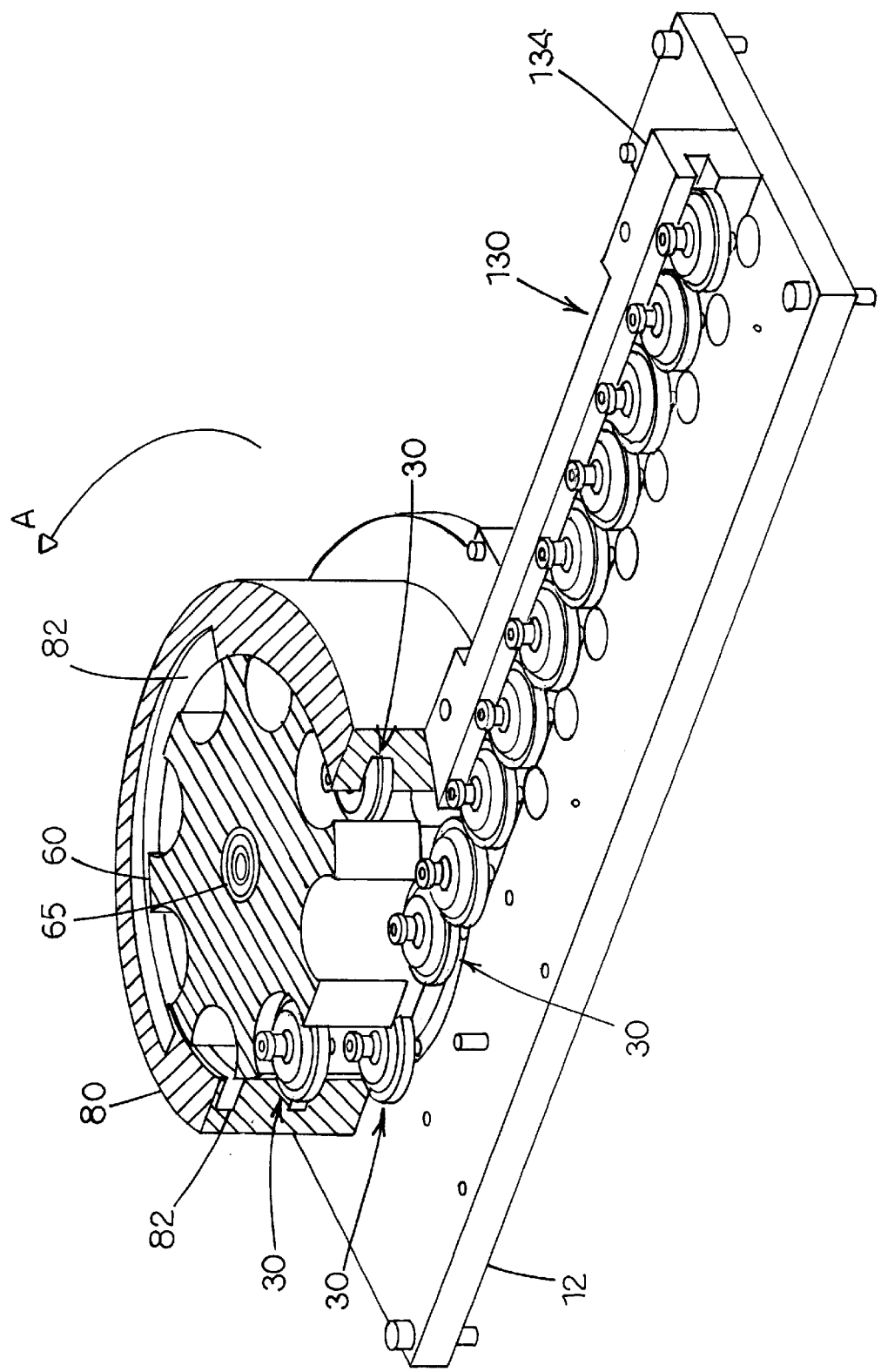
FIG. 5 is a detailed perspective view of a section of the filter changing apparatus illustrated in FIG. 1, wherein the filter unit separation assembly is shown in partial cutaway view and certain components of the filter changing apparatus have been removed to illustrate a helical path and subsequent lateral path traversed by a series of filter units during operation of the filter changing apparatus.

Referring to FIGS. 5, 9 and 10, and assuming for the sake of example that eight new filter units 30 are to replace eight old filter units 30, filter units 30 traveling along lateral track 130 continue to be advanced in indexing fashion through coupling sites $CS_1$–$CS_8$ by the urging of ensuing filter units 30. Filter unit position sensor 23 detects the presence of each filter unit 30 locking into and passing through first coupling site $CS_1$, in the manner described hereinabove. Accordingly, as each filter unit 30 passes through first coupling site $CS_1$, filter unit position sensor 23 sends a transduced signal to electronic control unit 200 to enable electronic control unit 200 to count the number of filter units 30 entering lateral track 130 (and hence the number of filter units 30 being loaded into clamping assembly 100). In addition, as each filter unit 30 advances into the next indexed coupling site $CS_2$–$CS_8$, one used filter unit 30 is pushed out from filter changing apparatus 10 through discharge end 138 of lateral track 130 and can then be collected in a waste receptacle if desired. When eight filter units 30 have been counted, electronic control unit 200 issues an appropriate control signal to deactivate filter separation assembly motor 67. At this point, due to the action of filter unit positioning slides 160 as described hereinabove, each filter unit 30 residing in lateral track 130 is positioned at a corresponding coupling site $CS_1$–$CS_8$ in proper alignment with fittings 108 and 112 of clamping assembly 100, as best illustrated in FIGS. 10–12. Finally, electronic control unit 200 causes clamping assembly 100 to mate fittings 32A and 34A of newly loaded filter units 30 with corresponding fittings 108 and 112 of clamping assembly 100, and a continuous fluid circuit is thereby reestablished with new filter units 30 automatically installed in-line.

It will be evident from the foregoing description that filter changing apparatus 10 is useful to transferring one or more filter units 30 from a stacked or columnar arrangement to an individualized or indexed, lateral side-by-side arrangement. In addition, the design of filter changing apparatus 10 and that of its various components as described hereinabove, as well as the interaction of the various components, ensures that the operations and functions performed by filter changing apparatus 10 are not adversely affected by varying situations expected to be encountered in the use of filter changing apparatus 10. Such situations include (1) a plurality of magazines 40 loaded in magazine carrousel 55 with differing numbers of filter units 30; (2) magazines 40 being absent from one or more bores 70A of barrel portion 70; and (3) the occasional failure of a lowermost filter unit 30 of a stack to drop down into entry point 84 of base block 80 during rotation of filter separation assembly 50.

It will be further understood that various details of the invention may be changed without departing from the scope of the invention. Furthermore, the foregoing description is for the purpose of illustration only, and not for the purpose of limitation—the invention being defined by the claims.

What is claimed is:

1. A filter dispensing apparatus comprising:
   (a) a rotary member having a longitudinal axis; and
   (b) a stationary member including an annular interior surface disposed in coaxial relation to the rotary member, an inlet opening, an outlet opening disposed at an axial distance from the inlet opening, and a channel formed on the interior surface, the channel running along a generally helical path with respect to the longitudinal axis with a varying pitch of the channel increasing with respect to an axial length of the interior surface, and the channel communicating with the inlet opening and the outlet opening.

2. The filter dispensing apparatus according to claim 1 comprising a filter storage device supported by the rotary member and communicating with the inlet opening.

3. The filter dispensing apparatus according to claim 1 comprising a barrel member mounted to the rotary member above the stationary member and including a bore communicating with the inlet opening.

4. The filter dispensing apparatus according to claim 3 comprising a filter storage device mounted to the barrel member bore and including an open end disposed in the bore.

5. A filter dispensing apparatus comprising:
   (a) a rotatable shaft;
   (b) a filter handling device secured to the shaft and defining a first filter path; and
   (c) a filter separation device having an annular interior surface fixedly disposed in coaxial relation to the shaft, the filter separation device including an entry location disposed in communication with the first filter path, an exit location disposed at an axial distance from the entry location, and a channel formed on the interior surface and defining a second filter path, the channel running along a generally helical orientation with respect to the shaft with a varying pitch of the channel increasing with respect to an axial length of the interior surface, and the channel communicating with the entry location and the exit location.

6. The filter dispensing apparatus according to claim 5 wherein the filter handling device includes a rotary member, the rotary member at least partially defining the first filter path and including a section circumscribed by the annular interior surface.

7. The filter dispensing apparatus according to claim 5 wherein the filter handling device includes a barrel member disposed above the annular interior surface, the barrel member at least partially defining the first filter path and including a bore communicating with the entry location.

8. The filter dispensing apparatus according to claim 5 comprising a filter storage device supported by the filter handling device and including an open end disposed in communication with the entry location.

9. An apparatus for replacing a filter in a fluid line comprising:
   (a) a rotatably movable filter handling device defining a generally downward first filter path;
   (b) a stationary filter handling device defining a generally helical second filter path communicating with the first filter path;
   (c) a filter guiding device defining a third filter path, the third filter path communicating with the second filter path and oriented in a generally transverse relation to the first filter path; and
   (d) a filter clamping device communicating with a fluid line and adapted for releasable engagement with a filter disposed in the filter guiding device.

10. An apparatus for replacing a filter in a fluid line comprising:
    (a) a filter storage device;
    (b) a filter clamping device; and
    (c) a filter conveying device for conveying a plurality of filters from a stacked arrangement in the filter storage device, through a generally helical path, and to a sequential, lateral arrangement in the filter clamping device.

11. An apparatus for connecting a plurality of filters to a plurality of corresponding fluid lines comprising:
    (a) a filter storage device;
    (b) a filter clamping device including a plurality of pairs of inlet and outlet fittings, each pair of inlet and outlet fittings adapted for communication with a fluid line, the filter clamping device adapted to impart a total clamping force to a plurality of filters received in the filter clamping device to connect each filter, under influence of a portion of the total clamping force, in fluid communication with a corresponding one of the pairs of inlet and outlet fittings;

(c) means for conveying the plurality of filters from the filter storage device to the filter clamping device; and (d) means for distributing the total clamping force to the plurality of filters to reduce variations among the portions of the total clamping force imparted to each filter by the filter clamping device.

12. An apparatus for connecting a filter to a fluid line comprising:

(a) a filter storage device;

(b) a filter clamping device including an inlet fitting and an outlet fitting, the inlet and outlet fittings adapted for communication with a fluid line;

(c) means for conveying a filter having first and second fittings from the filter storage device to the filter clamping device; and (d) a filter positioning device for aligning the first fitting with the inlet fitting and the second fitting with the outlet fitting, the filter positioning device comprising a spring-biased, slidable member adapted for engaging the filter.

13. The apparatus according to claim 9 wherein the stationary filter handling device comprises an annular interior surface, an inlet opening, an outlet opening spaced from the inlet opening, and a channel formed on the annular interior surface, the annular interior surface disposed in coaxial relation to the rotatably movable filter handling device, and the channel defining the generally helical second filter path and communicating with the inlet opening and the outlet opening.

14. The apparatus according to claim 9 comprising a filter positioning slide movable generally transversely in relation to the third filter path.

15. The apparatus according to claim 9 wherein the filter clamping device comprises an actuator, a first arm and a second arm, the first arm comprising a first fitting disposed in movable relation to the first arm, the second arm disposed in movable engagement with the actuator and comprising a second fitting disposed in movable relation to the second arm, and wherein the actuator is adapted to adjust an axial distance between the first arm and the second arm.

16. The apparatus according to claim 10 wherein the stacked arrangement of filters is oriented along a first direction, and the lateral arrangement of filters is oriented along a second direction generally perpendicular to the first direction.

17. The apparatus according to claim 16 wherein the helical path turns about an axis of rotation parallel to the first direction.

18. The apparatus according to claim 10 wherein the filter conveying device comprises an interior surface, an inlet opening, an outlet opening spaced from the inlet opening, and a channel formed on the interior surface, and wherein the channel defines the generally helical path and communicates with the inlet opening and the outlet opening.

19. The apparatus according to claim 10 wherein the filter clamping device comprises an actuator, a first arm and a second arm, the first arm comprising a first fitting disposed in movable relation to the first arm, the second arm disposed in movable engagement with the actuator and comprising a second fitting disposed in movable relation to the second arm, and wherein the actuator is adapted to adjust an axial distance between the first arm and the second arm.

20. The apparatus according to claim 11 wherein the conveying means comprises an interior surface, an inlet opening communicating with the filter storage device, an outlet opening communicating with the filter clamping device, and a channel formed on the interior surface, and wherein the channel defines a generally helical path and communicates with the inlet opening and the outlet opening.

21. The apparatus according to claim 11 wherein the filter clamping device comprises an actuator, a first arm, a second arm communicating with the actuator and movable by the actuator in relation to the first arm, and wherein the inlet fittings are movably mounted to the first arm and the outlet fittings are movably mounted to the second arm.

22. The apparatus according to claim 21 comprising a filter track interposed between the first arm and the second arm and defining a plurality of filter coupling sites, wherein each inlet fitting is disposed on one side of each respective coupling site and each outlet fitting is disposed on an opposing side of each respective coupling site.

23. The apparatus according to claim 22 comprising a plurality of filter positioning devices corresponding to the plurality of pairs of inlet and outlet fittings, each filter positioning device movable in a direction generally transverse to the filter track at a respective coupling site.

24. The apparatus according to claim 11 wherein the force distributing means comprises a plurality of springs, each spring engaging a respective inlet fitting and biasing the inlet fitting away from the second arm.

25. The apparatus according to claim 12 wherein the conveying means comprises an interior surface, an inlet opening communicating with the filter storage device, an outlet opening communicating with the filter clamping device, and a channel formed on the interior surface, and wherein the channel defines a generally helical path and communicates with the inlet opening and the outlet opening.

26. The apparatus according to claim 12 wherein the filter clamping device comprises an actuator, a first arm, a second arm communicating with the actuator and movable by the actuator in relation to the first arm, wherein the inlet fitting is movably mounted to the first arm and the outlet fitting is movably mounted to the second arm, and wherein the filter positioning device is slidable between the first arm and the second arm.

* * * * *